US009251685B2

(12) United States Patent
Patil et al.

(10) Patent No.: US 9,251,685 B2
(45) Date of Patent: Feb. 2, 2016

(54) SYSTEM AND METHOD FOR MEDICAL DIAGNOSIS USING GEOSPATIAL LOCATION DATA INTEGRATED WITH BIOMEDICAL SENSOR INFORMATION (75) Inventors: Sandeep R. Patil, Pune (IN); John G. Musial, Newburgh, NY (US); Dhaval K. Shah, Gujarat (IN); Abhinay R. Nagpal, Pune (IN)

(73) Assignee: International Business Machines Corporation, Armonk, NY (US)

( * ) Notice: Subject to any disclaimer, the term of this patent is extended or adjusted under 35 U.S.C. 154(b) by 1285 days.

(21) Appl. No.: 13/029,929

(22) Filed: Feb. 17, 2011

(65) Prior Publication Data
US 2012/0215455 A1    Aug. 23, 2012

(51) Int. Cl.
*A61B 5/00* (2006.01)
*G08B 21/02* (2006.01)
*G06F 19/00* (2011.01)
*A61B 5/11* (2006.01)

(52) U.S. Cl.
CPC .............. *G08B 21/02* (2013.01); *A61B 5/0022* (2013.01); *G06F 19/3418* (2013.01); *G06F 19/3493* (2013.01); *A61B 5/1112* (2013.01)

(58) Field of Classification Search
CPC  A61B 5/0022; A61B 5/1112; G06F 19/3493; G08B 21/02
USPC .................. 702/141, 142, 149, 176, 178, 188
See application file for complete search history.

(56) References Cited

U.S. PATENT DOCUMENTS

| 7,221,928 | B2 | 5/2007 | Laird et al. |
| 7,399,276 | B1 | 7/2008 | Brown et al. |
| 7,609,155 | B2 | 10/2009 | Hinkamp |

(Continued)

FOREIGN PATENT DOCUMENTS

| CN | 1555204 A | 12/2004 |
| JP | 2006-334369 A | 12/2006 |

OTHER PUBLICATIONS

Keeling, Matthew, "The Mathematics of Diseases", +Plus Magazine, Issue 14, http://plus.maths.org/issue14/features/diseases/, printed on Feb. 9, 2011.

(Continued)

*Primary Examiner* — Manuel L Barbee
(74) *Attorney, Agent, or Firm* — Cahn & Samuels, LLP (57) ABSTRACT In at least one embodiment, a method and system for accumulating geospatial location data and biomedical data for an individual during his/her travels is provided. In at least one embodiment, a device uses at least one location signal to determine geospatial data and receives a plurality of biomedical signals with both data types being stored for possible later retrieval for providing a diagnosis for the individual if a medical condition arises. An embodiment of the invention provides a method of operation of a device having at least a memory and a communications module where the method includes receiving at least one location signal with the communications module; storing geospatial data obtained at least from the at least one location signal with a time stamp in memory; receiving a plurality of biomedical signals over time from at least one sensor with the communications module; storing biomedical data from the received biomedical signal with a time stamp in memory; and repeating the receiving at least one location signal and storing geospatial data from the at least one location signal in different geographic locations.

24 Claims, 6 Drawing Sheets

(56) References Cited

U.S. PATENT DOCUMENTS

| | | |
|---|---|---|
| 7,648,463 B1 | 1/2010 | Elhag et al. |
| 8,666,768 B2 | 3/2014 | Ji et al. |
| 8,753,273 B1 | 6/2014 | Lau et al. |
| 2002/0109600 A1 | 8/2002 | Mault et al. |
| 2003/0204130 A1 | 10/2003 | Colston, Jr. et al. |
| 2005/0131740 A1 | 6/2005 | Massenzio et al. |
| 2006/0036619 A1 | 2/2006 | Fuerst et al. |
| 2006/0066449 A1 | 3/2006 | Johnson |
| 2006/0089542 A1 | 4/2006 | Sands |
| 2007/0046476 A1 | 3/2007 | Hinkamp |
| 2007/0232942 A1 | 10/2007 | Quy |
| 2007/0273499 A1 | 11/2007 | Chlubek et al. |
| 2010/0056341 A1* | 3/2010 | Ellis et al. .................. 482/9 |
| 2010/0088107 A1 | 4/2010 | Ur et al. |
| 2011/0025493 A1 | 2/2011 | Papadopoulos et al. |
| 2011/0145162 A1 | 6/2011 | Vock et al. |
| 2011/0161096 A1 | 6/2011 | Buehler et al. |
| 2012/0084092 A1* | 4/2012 | Kozuch et al. .................. 705/2 |
| 2012/0095779 A1 | 4/2012 | Wengrovitz et al. |
| 2013/0086201 A1 | 4/2013 | Legge |
| 2013/0120140 A1 | 5/2013 | Patil et al. |

OTHER PUBLICATIONS

Naadsm, "About NAADSM," http://ww.naadsm.org, printed on Feb. 8, 2011.

Romer, Joshua J., "No. 1 Smartphones," IEEE Spectrum, Jan. 2011, pp. 28-31, vol. 48, No. 1, North American edition.

Wong, Weng-Keen, "What's Strange About Recent Events (2003)," AutonLab, http://www.autonlab.org/autonweb/14637.html, printed on Feb. 8, 2011.

Wong, Weng-Keen, et al., "What's Strange About Recent Events (WSARE): An Algorithm for the Early Detection of Disease Outbreaks", Journal of Machine Learning Research, 2005, pp. 1961-1998, vol. 6.

Yu, Hwanjo, et al., "Privacy-Preserving SVM using Nonlinear Kernels on Horizontally Partitioned Data", SAC '06, Apr. 23-27, 2006, pp. 603-610.

* cited by examiner

| John Doe April Travels and Biomedical Readings | | | | |
|---|---|---|---|---|
| | Location A | Location B | Location C | Location D |
| Dates | 4/1/10-4/3/10 | 4/3/10-4/4/10 | 4/4/10-4/7/10 | 4/7/10-present |
| Length of time | 2 days | 1 day | 3 days | 1 day |
| Temperature | 98 | 99.3 | 100 | 102 |
| Blood pressure | 122/81 | 123/82 | 120/78 | 122/80 |
| Pulse | 78 | 74 | 82 | 80 |
| WHO | H1N1, Dengue | | | |

SYSTEM AND METHOD FOR MEDICAL DIAGNOSIS USING GEOSPATIAL LOCATION DATA INTEGRATED WITH BIOMEDICAL SENSOR INFORMATION

I. FIELD OF THE INVENTION

The present invention in at least one embodiment provides a system and method for monitoring and storing one or more biomedical readings of an individual along with a correlated temporally-based, geospatial location data such that known health issues and diseases associated with the geospatial locations visited by the individual can be used to assist medical professionals with diagnosis of the individual.

II. BACKGROUND OF THE INVENTION

Modern medical professionals have to contend with illnesses from all over the world. Due to the speed and accessibility of international travel, the spread of disease can be very fast and prolific. When performing a diagnosis, medical doctors often take into account diseases that they are familiar with and the diseases that they believe to be common, e.g., to the presenting symptoms. This information can be sufficient to correctly diagnose a patient, however this does not hold true for all cases. For example, doctors may be unaware of a known illness or outbreak in a distant location recently traveled to by a patient, which may result in a misdiagnosis that could have been easily made given the knowledge of the illness or outbreak. Further, doctors are known to be influenced by recent cases that they have seen and consequently more rare or atypical illnesses with similar symptoms to a common, recently observed case presents a heightened possibility for misdiagnosis.

III. SUMMARY OF THE INVENTION

An embodiment of the invention provides a method of operation of a device having at least a memory and a communications module where the method includes receiving at least one location signal with the communications module; storing geospatial data obtained at least from the at least one location signal with a time stamp in memory; receiving a plurality of biomedical signals over time from at least one sensor with the communications module; storing biomedical data from the received biomedical signal with a time stamp in memory; and repeating the receiving at least one location signal and storing geospatial data from the at least one location signal in different geographic locations. In a further embodiment, the method further includes determining the geographic location of the device based on contemporaneously received location signals, the geographic location is the geospatial data stored. In a further embodiment, the method further translates the location signal into a geographic location for storage as the geospatial data. In a further embodiment, the method further receives the series of biomedical signals from one sensor at predetermined times. In a further embodiment, the method further receives from memory the predetermined time period for obtaining a biomedical signal from the one sensor, determines based on the time the last biomedical signal was received when to request the next biomedical signal from the one sensor, and requests the biomedical signal from the one sensor in response to the time determined to request the next biomedical signal from the one sensor. In a further embodiment, the method further determines when a new geographic location has been reached by the device, requests a biomedical signal from each sensor associated with the device, and stores the received at least one biomedical signal with a time stamp and the geographic location in memory. In a variety of embodiments the data is stored in a database resident in memory of the device. In at least one embodiment, the method transfers the geospatial data, the biomedical data and associated time stamp data to an external computer. In at least one embodiment, the method converts the biomedical signals into biomedical data representing a biomedical reading for the sensor that provided the biomedical signal. In a further embodiment, the method further correlates the biomedical readings with the geospatial data based on the respective time stamps; derives at least one geographic location from the geospatial data; retrieves supplemental data for the at least one geographic location present in the data for time periods that the biomedical readings were gathered for that respective geographic location; and displays an interface to provide the correlated data and supplemental data to a user. Further to the previous embodiment, displaying includes displaying a map showing where the individual traveled recently with each discrete geographic location illustrated having a selection element for displaying information about the individual including a name of that geographic location, time information about the geographic location, at least one biomedical reading associated with that geographic location, and supplemental data for that geographic location.

An embodiment of the invention provides a method including receiving a data set for an individual having geospatial data including a time stamp and biomedical readings correlated with at least one time stamp, the data set representative of recent travels of the individual; correlating the biomedical readings with the geospatial data based on the respective time stamps; retrieving supplemental data for the at least one geographic location corresponding to the geospatial data for time periods that the biomedical readings were gathered for that geographic location; and displaying an interface to provide the correlated data and supplemental data to a user.

An embodiment of the invention provides a device including a communications module; a location module connected to the communications module, the location module processes information received by the communications module associated with location of the device; a monitoring module connected to the communications module, the monitoring module processes information received by the communications module associated with biomedical readings received from at least one external sensor; and a memory connected to the location module and the monitoring module, the memory stores data outputted by the location module and the monitoring module. In at least one embodiment, the device further includes a clock connected to the monitoring module, and wherein the monitoring module determines when to have the communications module request at least one biomedical signal from the at least one external sensor based on time information received from the clock and at least one sampling period stored in the memory. In a further embodiment, the device also includes a display; and an interface engine connected to the display and the memory, the interface engine retrieves data from the memory including stored biomedical readings, geospatial location data representing at least one geographic location, and associated temporal data to display a map on the display showing where the individual traveled recently with each discrete geographic location illustrated having a selection element for displaying information about the individual including a name of that geographic location, time information about the geographic location, at least one biomedical reading associated with that geographic location, and supplemental data for that geographic location. In at least one further embodiment, the device further includes a medical facility detector connected to the memory and the location module, the medical facility detector determines whether the device is present at a medical facility based in part upon the geographic location determined by the location module and when present at the medical facility, the medical facility detector allows access to biomedical and geospatial data stored in the memory.

An embodiment of the invention provides a method of operation of a device having memory and a communications module where the method includes receiving a plurality of biomedical signals over time from at least one sensor with the communications module; storing data from the received biomedical signal with a time stamp in memory; obtaining at least one location signal for each received biomedical signal with the communications module; determining geospatial data based on the at least one obtained location signal, storing geospatial data in memory correlated with the data from the received biomedical signal; and repeating the receiving at least one location signal and storing geospatial data from the at least one location signal in different geographic locations.

An embodiment of the invention provides a computer program product for content management, the computer program product including: a computer readable storage medium; first program instructions to obtain at least one location signal; second program instructions to translate the at least one location signal into a geographic location and store the geographic location in memory; third program instructions to receive a plurality of biomedical signals over time from at least one sensor; fourth program instructions to translate each received biomedical signal into a biomedical reading and store the biomedical reading with a time stamp in memory; and the first program instructions, the second program instructions, the third program instructions, and the fourth program instructions are stored on the computer readable storage medium.

IV. BRIEF DESCRIPTION OF THE DRAWINGS

The present invention is described with reference to the accompanying drawings. In the drawings, like reference numbers indicate identical or functionally similar elements. The use of cross-hatching and shading within the drawings is not intended as limiting the type of materials that may be used to manufacture the invention.

Given the following enabling description of the drawings, the system and method should become evident to a person of ordinary skill in the art.

V. DETAILED DESCRIPTION OF THE DRAWINGS

The present invention in at least one embodiment provides a system and method for real-time monitoring, tracking, and storing of information related to the biomedical condition and health characteristics of an individual with respect to date, time, and geographic location such that the causes and/or sources of illnesses and/or diseases can be more efficiently and reliably determined by medical professionals. In at least one embodiment, the present invention allows the stored biomedical data of the individual to be used with or mapped to known health issues and/or diseases associated with the geographic locations visited by the individual. The stored biomedical data provides medical professionals with a full and clear representation of the biomedical history of the individual along with temporally related geospatial information such that known health issues and illnesses of particular locations can be quickly and reliably identified.

The present invention in at least one embodiment provides a medical diagnosis system and method that monitors and stores biomedical readings of an individual with respect to date, time, and geographic location. The present invention in at least one embodiment enables the improved diagnosis of illnesses and/or diseases to be made based on the logged health characteristics of the individual and the known health issues and diseases associated with the geographic locations visited by the individual. In at least one further embodiment, the stored data can provide relevant information to medical professionals when the individual is unable to communication, for example, when he/she is unconscious or speaks a different language.

Figure 1:
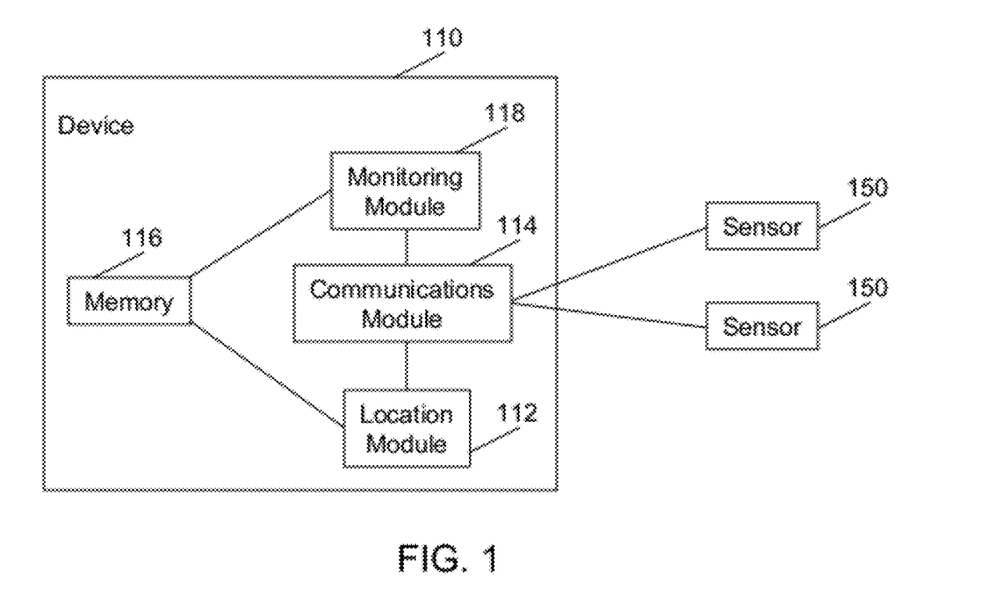
FIG. 1 illustrates an embodiment according to the invention.

FIG. 1 illustrates an example of a system in accordance with an embodiment of the present invention for monitoring and gathering the biomedical condition of an individual with respect to the temporal geospatial location data for the individual. The illustrated example includes a device 110 in communication with one or more biomedical sensors 150. The device 110 includes a location module 112, a communications module 114, a memory (or storage) 116 that in at least one embodiment includes a database, and a monitoring module 118. Examples of the device 110 include mobile phones, smart phones, personal digital assistants (PDAs), cameras, electronic book readers, tablet computers, netbooks, laptops, mp3 or other music players, global positioning system (GPS) devices, application specific devices, and the like that include computing capability such as a processor programmed to run the modules.

The location module 112 receives signals from the communications module 114 for use in determining location. Examples of these types of signals include GPS satellite signals, signals from nearby cellular telephone towers, and radio frequency identification (RFID) (or similar type) signal data identifying location. In an embodiment that uses signals from GPS satellites and cellular telephone towers, those signals are processed by the location module 112 to identify the location where the device 110 is located based on relative signal strength received from at least two signal emitters. In an embodiment that uses the RFID signal or similar signal having that information, the signal itself will include information identifying the geographic location in which the device 110 is or passes through. An example of this type of signal is that a signal source present at a checkpoint identifying the city where the checkpoint is located. A further possible source of geospatial data is from a WLAN signal including identification information as to the location of a hub or router such as at a hotspot location where the IP address is converted into a geographical location of the hub/router. The location module 112 stores the geospatial location information into the memory 116 to be associated with biomedical readings.

The communications module 114 is preferably capable of supporting a variety of communications platforms and protocols such as wireless protocols, Bluetooth or other infrared short range wireless communication, Short Message Service (SMS) messaging, Multimedia Messaging Service (MMS), Global System for Mobile (GSM) communications standard, the Code Division Multiple Access (CDMA) communication, Global Positioning System (GPS), Worldwide Interoperability for Microwave Access (WiMAX), wireless local area networks, wire network connection, etc. The communications module 114 in at least one GPS embodiment is capable of communicating on one or more GPS communication platforms such as the United States NAVSTAR system, the Chinese Compass system, the French Galileo system, the Russian GLONASS system, and other similar systems. The communications module 114 also provides the connection to the sensors 150 associated with the individual being monitored. Examples of the connections to the sensors 150 include wireless and wired. The wireless connections in at least one embodiment would use existing protocols to establish the connection between the device 110 and the sensor 150. Alternatively, the sensor 150 could be connected to the device 110 with a cable or other wire. In a further embodiment, the device 110 may include a built-in sensor 150. In a still further embodiment, the data produced by the sensor 150 is read from a memory card or entered into the device 110 using, for example, the screen and/or keypad/keyboard on the device 110.

As illustrated, the device 110 further includes a monitoring module 118 in communication with the communications module 114. The communications module 114 provides the biomedical signals from the one or more sensors 150 to the monitoring module 118 for processing and interpretation of what the signal represents. In at least one embodiment, the communications module 114 also provides identification of the source of the biomedical signal to aid in interpreting the signal by the monitoring module 118. The data obtained from the signal is provided to the memory 116 for storage with a time-stamp representing the time the biomedical reading was obtained.

Figure 2:
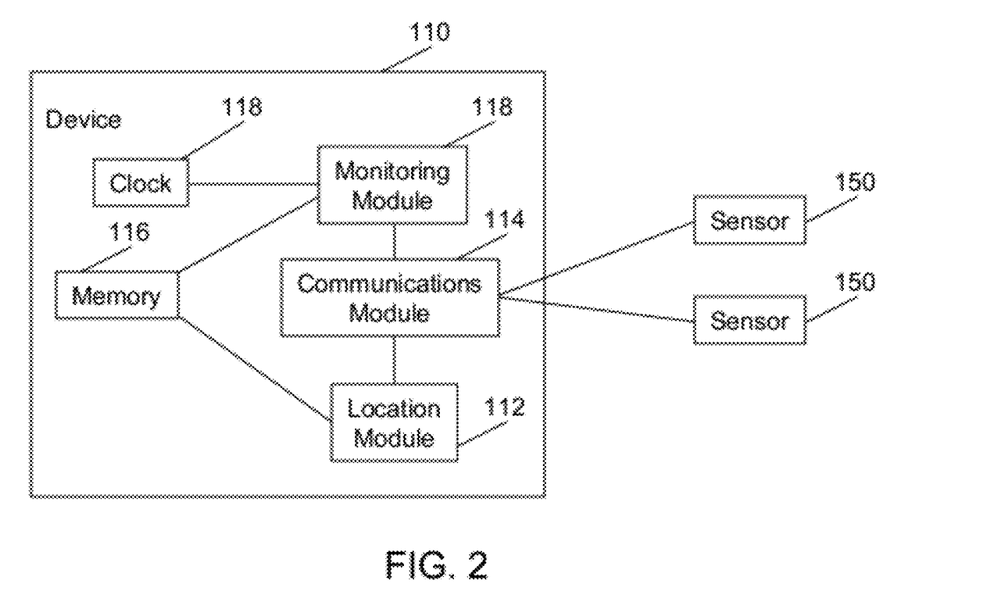
FIG. 2 illustrates another embodiment according to the invention.

In at least one embodiment, the monitoring module 118 pings one or more sensors 150 in communication with the device 110 to provide the current biomedical reading of the sensor 150 for storage in the memory 116. In this embodiment as illustrated in FIG. 2, the monitoring module 118 is in communication with a clock 220 and/or timer to provide a time signal to be used in determining whether a predetermined time has passed and at least one new biomedical reading is to be obtained from one or more sensors 150. In a further embodiment, the monitoring module 118 sets a predetermined time period between readings for each sensor 150 where the time periods may be the same for all sensors, the same for some sensors and different for at least one other sensor, or different for each of the sensors in communication with the communications module 114. The predetermined time periods may be stored in memory 116 for retrieval by the monitoring module 118. Once the predetermined time has been reached, the monitoring module 118 has the communications module 114 ping the relevant sensor(s) 150 for a reading(s). In at least one embodiment where the sensor 150 is built into the device 110 or the sensor 150 requires the individual to provide the reading, the monitoring module 118 provides an alert or other notification to the user that a reading is needed. Examples of an alert/notification include an audio queue like a beep, bell, or music through a speaker; a tactical queue like vibration of the device 110; a visual queue like a light; or some combination of these different queues.

In a still further embodiment, at least one predetermined time period is shorten when the reading from the associated sensor 150 changes in excess of a predetermined change for the particular sensor stored in the memory 116. An example of the predetermined change using temperature is a percentage change in temperature or a fixed amount such as two degrees over a period of time or between the two most recent temperature readings.

In another embodiment, the monitoring module 118 determines whether the most recent biomedical reading is substantially similar to the previous reading such that it can be omitted from being stored in memory 116 and that upon retrieval of the stored data the device 110 will insert the reading from the previous reading in time into any display or transfer of the information.

In at least one further embodiment, the monitoring module 118 is integrally incorporated into the communications module 114.

The memory (or storage) 116 is in communication with the location module 112 and the monitoring module 118 for storing the data produced by these two modules. In at least one embodiment, the data is stored in a database residing in the memory 116. The memory 116 provides storage of any predetermined time periods or changes used by the monitoring module 118 for those relevant embodiments. The temporally based information related to the biomedical reading(s) and geospatial location of the individual allows medical professionals to quickly and reliably access and use the information at a later time. This stored information greatly enhances the ability of medical professional to accurately diagnose illness and disease related to the individual by providing a full and clear temporal representation of the recent travel and health of the individual.

Once the stored information related to the recent travel and health of the individual is accessed, this information can be correlated with other information to assist with diagnosis. The correlation of the information can be done, for example, by a programmed external computer in embodiments where the data is transferred from the device 110 or by the communications module 114 (or a separate search module connected to the communications module 114 and the memory 116). Other sources of information (or supplemental data), such as health organization reports, may also be used including known illnesses, diseases, and health issues in the areas traveled to by the individual. In embodiments where the device 110 performs the search, the supplemental data may be stored in memory 116 and correlated to the geospatial location data. These reporting sources may include various entities that adhere to proscribed standards of reliability such as private medical facilities, e.g., hospitals and clinics, governmental organizations, e.g., the Centers for Disease Control and Prevention (CDC), and the World Health Organization (WHO), etc. The information obtained through these reporting sources may include, for example, current epidemic alerts, the scale of each active epidemic based on a standard, e.g., the phase level number, per location around the world, and the number of affected people reported. The alerts could be archived by the medical professional and searched using the geospatial information associated with the patient.

Figure 3:
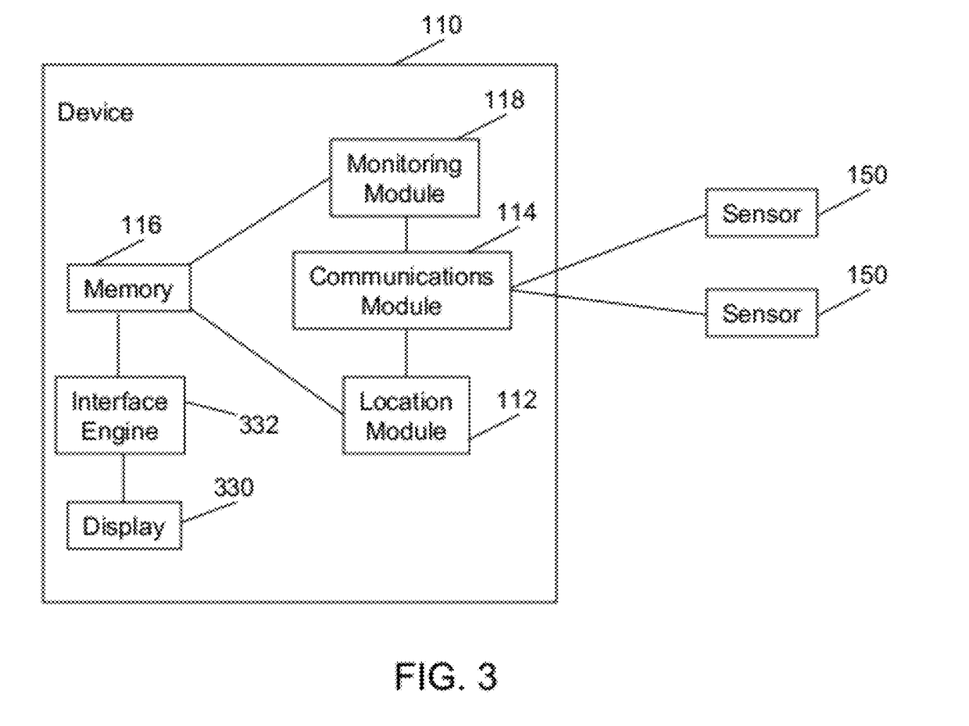
FIG. 3 illustrates a further embodiment according to the invention.

FIG. 3 illustrates a further embodiment according to the invention. The illustrated embodiment adds a display 330 and an interface engine 332 to the embodiment illustrated in FIG. 1. The interface engine 332 pulls data from the memory 116 to display data on the display 330. Examples of how the data may be displayed are discussed later in connection with FIGS. 9 and 10. The interface engine 332 retrieves the data from the memory 116 that includes, for example, biomedical readings, geospatial location data, and temporal information for the biomedical readings. In at least one further embodiment, the interface engine 332 also provides any supplemental data that is located during a search performed by the communications module 114.

At least one of the sensors 150 is a biomedical sensor(s) that monitors one or more physiological conditions, e.g., body temperature, sugar levels, breathing rate, pulse rate, heart rate, blood oxygenation, level of activity, blood pressure, etc. The sensors 150 may be, for example, non-invasively attached to the body or located in clothing of the individual and in communication with the device 110. In a further embodiment, at least one sensor 150 is implanted in the individual. In a still further embodiment, the sensor 150 is incorporated into the device 110. The communications module 114 of the device 110 is programmed to receive signals from the sensors 150 representative of at least one physiological condition to obtain a biomedical reading. The communications module 114 provides the signal to the monitoring module 118 for processing. The device 110 stores the received signals such that the temporal health of the individual can be determined later based on the stored information.

The sensors 150 for use as part of the system can take a variety of forms. Examples of biomedical sensors include: heart rate (or pulse) sensors, respiration sensors, oximeters, thermometers, blood glucose monitors, blood pressure cuff systems, actigraphs, and any combination of these sensors. One or more of these sensors could be built into the device 110 to have the individual grasp or place a thumb/finger on the sensor to detect, for example, pulse rate or temperature. The sensors also could be non-invasive and incorporated into clothing, placed on straps, or incorporated into wrist bands worn by the individual. In at least one embodiment, the sensor is incorporated into medical equipment used by the individual such as a Continuous Positive Airway Pressure (CPAP) machine or a pacemaker.

Figure 4:
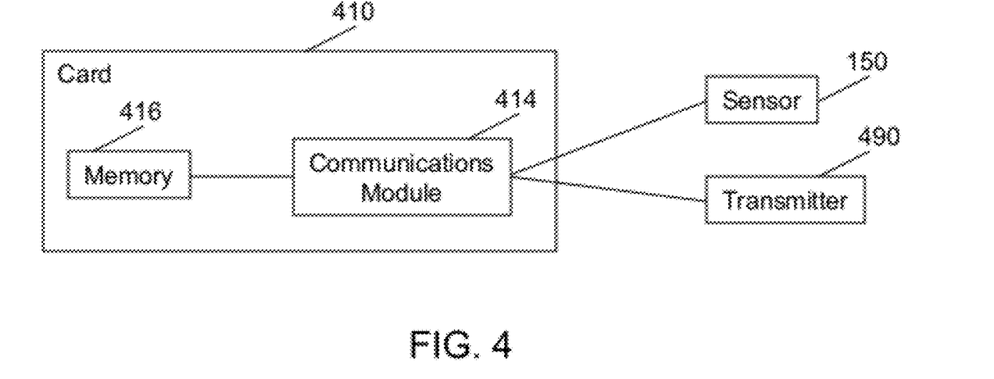
FIG. 4 illustrates a further embodiment according to the invention.
Figure 5:
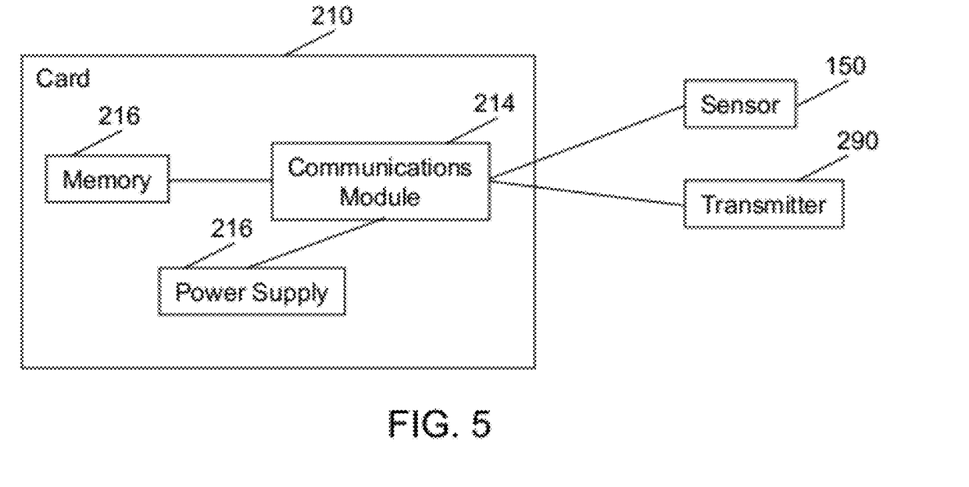
FIG. 5 illustrates a still further embodiment according to the invention.

In an alternative embodiment, the device 110 is replaced with a card 410 having a memory (or storage) 416 and a communications module 414 as illustrated in FIG. 4. In this embodiment, the card 410 will obtain location information from wireless transmitters or data readers/writers 490 that identify the location such as a RFID transmitter located at a passport control booth, a RFID transmitter at a toll booth or subway station, a card reader/writer at a passport control booth that is able to write to the card, etc. The sensors 150 in such a system would provide their respective readings wirelessly for storage on the card 410 to enable the data to be read (or transmitted) and correlated with temporal data and the respective geospatial data. In this embodiment, the sensors would have additional processing responsibility to provide the data in the appropriate form for storage on the card 410. The communications module 414 in this embodiment is a RFID (or other wireless) transmitter/receiver or a magnetic medium such as a magnetic strip built into the card 410. In a further embodiment, the card 410 would include a power supply 522 as illustrated in FIG. 5.

Figure 6:
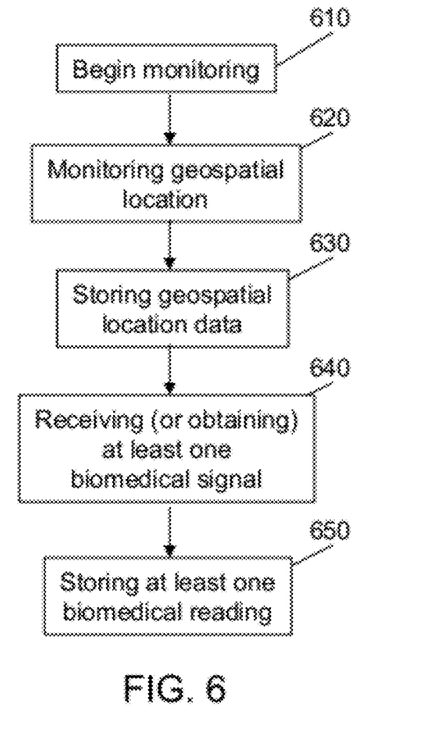
FIG. 6 illustrates an example of a method according to at least one embodiment of the invention.

FIG. 6 illustrates an example of a method in accordance with at least one embodiment of the present invention for monitoring and tracking the biomedical condition of an individual with respect to temporal geospatial location. The device 110, 410 is prompted to begin monitoring and storing geospatial and biomedical information (610).

The device 110, 410 monitors (620) and stores (630) the geospatial position of the device using, for example, GPS location, location determined based on proximity to cellular (or other wireless) towers (or access points), and entry and departure through identification check points such as passport (or border) control. Additional discussion of how the geospatial data and geographic location is obtained is discussed above in connection with the device and card embodiments.

At predetermined time periods (or continuously depending on the parameter being measured), the device 110, 410 receives (or obtains) at least one biomedical signal (640) and stores at least one biomedical reading (or parameter) of the individual (650) based on the signal from one or more biomedical sensors 150 associated with the device 110, 410 as discussed above. The sampling rate in a further embodiment is set and/or adjusted based on the advice of one or more medical professionals. In at least one embodiment, the device 110 pings the at least one biomedical sensor to provide the current reading of the parameter it is measuring. The timing of the monitoring can be at predetermined intervals such as hourly, every few hours, daily, weekly, etc. The timing can vary between biomedical readings being monitored by the device 110, for example, the temperature may be recorded every six hours while blood pressure is measured daily. In at least one embodiment, the frequency of monitoring of a biomedical reading changes if the change between the two most readings is in excess of a predetermined threshold. In at least one embodiment, the trigger for pinging the at least one biomedical sensor 150 is based on a change in geographic location such as entering/leaving a population center, city, or country. In at least one embodiment, the device 110 stores the biomedical data only when it is different from the previous reading, for example, when it changes or changes in excess of a predetermined threshold for the biomedical parameter being measured resulting in reduced storage requirements in the device from a reduction in data. The biomedical data is associated with the geospatial data.

Each entry of data, in at least one embodiment, is time stamped by the device. The time used could, for example, be the local time of where the individual is located, the time of where the individual lives, or a standard time such as Greenwich Mean Time. The monitoring of biomedical parameters and time stamping are repeated based on the timing of the biomedical parameter monitoring. The determination of geographic location can occur, for example, in conjunction with the biomedical reading monitoring, be continuously checked, be checked at predetermined times, or done on an ad hoc basis such as manual entry of the data or manual request by the individual.

Figure 7:
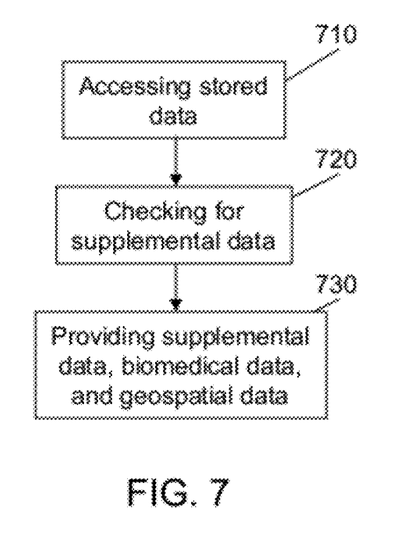
FIG. 7 illustrates an example of another method according to at least one embodiment of the invention.

FIG. 7 illustrates an example of a method in accordance with an embodiment of the present invention for diagnosing the cause of the illness and/or the disease. An individual making use of an embodiment described above feels ill seeks the care of a medical professional.

The medical professional is granted access to the stored biomedical data and geospatial location information related to the individual (710) and performs an analysis of the stored information in an effort to determine the location of infection. The medical professional is granted access to the stored biomedical and geospatial location data through, for example, the device 110 used by the individual or by downloading the information from the device 110 or the card 410 to a computer for reviewing the information.

The medical professional checks (or searches) reports of known illnesses and diseases (or supplemental data) provided by health organizations and other trusted sources (720). The checking of the report in at least one embodiment the medical professional causes a search to be done using the geospatial location data to select the relevant alerts and further limits the search results based on the temporal information. In an embodiment where the data is downloaded, the downloading of the data may trigger a search to be performed by the computer (or other processor system) that has downloaded the data. In a further embodiment, the geospatial location data is converted into a geographic place name such as a region or city to correlate with the supplemental data.

The medical professional is then able to crosscheck relevant reports and rare diseases with corresponding symptoms manifested in the individual by reviewing the information provided (730), for example, in an interface similar to that shown in FIGS. 5 and 6 by the computer or the device 110. The medical professional uses the provided information to assist in making a diagnosis based on the provided information.

An example of a known analytical method that would be suitable for the disclosed method is Multiple Correspondence Analysis (MCA). MCA is a data analysis technique for nominal or categorical data, used to detect and represent underlying structures in a data set. It does this by representing data as points in a low-dimensional Euclidean space. Associations between variables are uncovered by calculating the chi-square distance between different categories of the variables and between the individuals (or respondents). These associations are then represented graphically as "maps".

Figure 8:
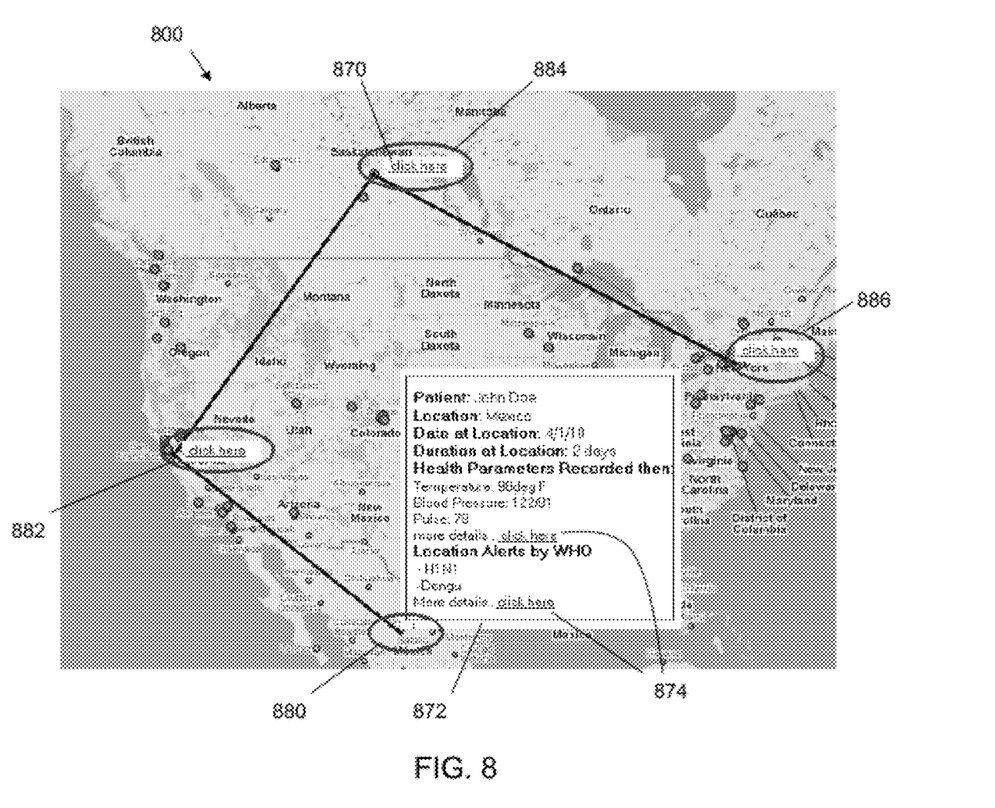
FIG. 8 illustrates an example of an interface embodiment according to at least one embodiment of the invention.

FIG. 8 illustrates an example of an example interface in accordance with at least one embodiment of the present invention as discussed above with respect to FIG. 7. FIG. 8 depicts a graphical representation 800 of the health and geospatial location information of an individual stored by the device 110, 410. The graphical representation 800 provides a depiction of the temporal health and geospatial location information of the individual such that the correlated information can be used by a medical professional(s) to perform a more accurate diagnosis of the cause(s) for the illness and/or the disease inflicting the individual (or patient). By viewing the graphical representation 800, the medical professional(s) can quickly determine the recent travel of the individual and gain possible insight into the recent health of the individual. The illustrated biomedical readings can be representative readings such as an average for that biomedical parameter, a median of the readings at that geographic location for that biomedical parameter, and a range with the end points representing the lowest and the highest readings for that biomedical parameter for that geographic location.

The graphical representation 800 illustrated in FIG. 8 shows that the individual recently visited four locations including Location A, Location B, Location C, and Location D depicted as 880, 882, 884, and 886, respectively. One of ordinary skill in the art will appreciate based on this disclosure that the number of locations could be other than four as used in this example. In the illustrated interface for example purposes: Location A represents a location in Mexico; Location B represents San Francisco, Calif., US; Location C represents Prince Albert, Saskatchewan, Canada; and Location D represents Syracuse, N.Y., US. The geographic location may be set to provide the country, state, and city or the exact positional coordinates such as the latitude and the longitude. By clicking on links (or selection element) 870 associated with each of the respective locations the computer used by the medical professional or the device 110 provides the medical professional with additional information 872 related to that location. For example, the link at Location A—Mexico indicates that the patient, John Doe, visited Mexico on Apr. 1, 2010 for a period of two (2) days. The stored biomedical condition of the patient includes a temperature of 98 degrees Fahrenheit, a blood pressure of 122/81, and a pulse of 78. The health alerts reported by the World Health Organization (WHO) for this location on that date is shown to be H1N1 (Influenza A virus) and Dengue virus (DENV). The medical professional may also access additional stored health information and location alerts by accessing provided links 874. This information assists the medical professional in quickly and accurately performing clinical diagnosis of the individual. The medical professional may then report any diagnosed illnesses or diseases including location(s) to a central collection entity.

In a further embodiment, the system and method include the ability to limit the amount of medical information retained in memory. One way to accomplish this is to allow the individual to set a time limitation such that medical data older than a threshold is deleted. Examples of the threshold include, but are not limited to, a few days, one or more weeks, a month, three months, four months, six months, a year, multiple years, etc. A second way to accomplish this is to allow the individual to set a number of locations where only the most recent locations traveled to our retained, for example a number following in one of these ranges (including the end points): 1-50, 2-25, 1-10, 2-5, and 2-4. A third way to accomplish this is to use a hybrid approach between the two other ways using the way that would provide the smallest or the largest data set.

Figure 9:
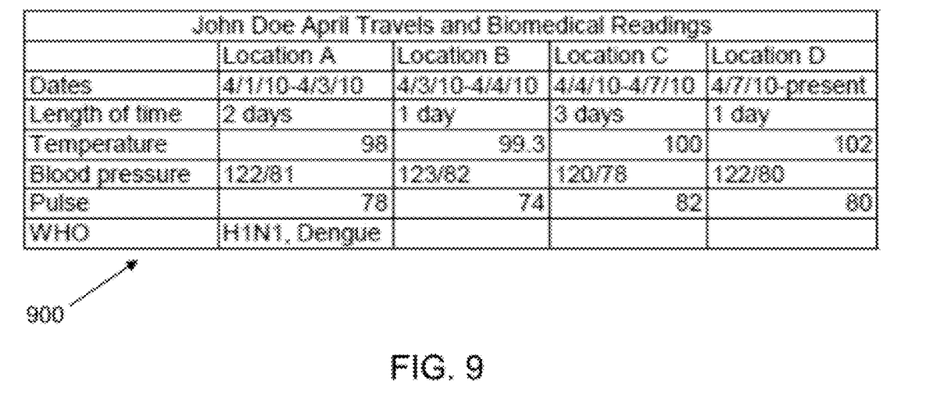
FIG. 9 illustrates another example of an alternative view according to at least one embodiment of the invention.

FIG. 9 illustrates an alternative interface for use with at least one embodiment of the present invention as depicted in FIG. 8. FIG. 9 depicts a table 900 of the tracked health and geospatial location information of an individual. The table 900 provides an alternative depiction of the temporal health and geographic location of the individual over a period of time. The table 900 allows the correlated information to be viewed and used by medical professions to perform a more accurate diagnosis of the cause(s) of the illness and/or the disease. By viewing the table 900, medical professionals can quickly compare the various recently visited locations and health of the patient by being able to view how the stored medical readings change over time (although a table is illustrated, this embodiment could illustrate line graphs, bar graphs or other pictorial representation of the underlying data). The table 900 provides various rows and columns of relevant information including, for example, the Location, Date, Duration, Health Parameters, Other Health Parameters, WHO Alerts, and Other Alerts. The table 900 is organized based on location, for illustration purposes the locations include Location A—Mexico, Location B—San Francisco, Location C—Saskatchewan, and Location D—New York from FIG. 8. Alternatively, the rows and columns could be switched with each other from that shown in FIG. 9 along with a different set of data being provided depending on the available data from the device 110, 410. As with the previous illustrated interface from FIG. 5, the same type of summaries could be used in the illustrated table.

The following scenario illustrates the usefulness of at least one embodiment using the data obtainable by the interfaces illustrated in FIGS. 8 and 9, the Mexican government or some other health organization, e.g., the World Health Organization (WHO), issue a health alert for Dengue virus and H1N1 in Mexico that were in effect on Apr. 1, 2010. Patient John Doe traveled to Mexico on Apr. 1, 2010 for two (2) days. The patient made stops in San Francisco, Calif. and Prince Albert, Saskatchewan before returning home to Syracuse, N.Y. on Apr. 7, 2010. The patient began to feel ill during his trip and visited a doctor in his hometown on Apr. 8, 2010. The doctor accesses the stored information of the patient and upon receiving the alerts realizes that the patient is exhibiting symptoms consistent with the alert for the H1N1 virus. The doctor is able to quickly and reliably diagnosis John Doe as having been exposed to the H1N1 virus while in Mexico and provide prognosis for recovery.

Another scenario illustrating the usefulness of at least one embodiment, John Doe visits Mexico on Apr. 1, 2010. There is a slight change in his blood pressure but he does not realize the change. After leaving Mexico John Doe travels to the United Kingdom where he gets very little sleep and feels a bit uneasy. John Doe then returns to the United States and his condition worsens. John Doe then visits his doctor. Upon reviewing the stored biomedical condition and geospatial location information related to John Doe, the doctor realizes that John Doe visited western Mexico on Apr. 1, 2010, that there was a slight increase in his blood pressure on that date and there was a health alert for Dengue virus in effect at that time. The system provides the doctor with the exact biomedical and location information related to John Doe including known diseases from regions to which he traveled. Utilizing this information, the doctor realizes that the onset on Dengue was the likely cause of the increase in blood pressure and avoids a misdiagnosis based on a lack of sleep and travel.

Figure 10:
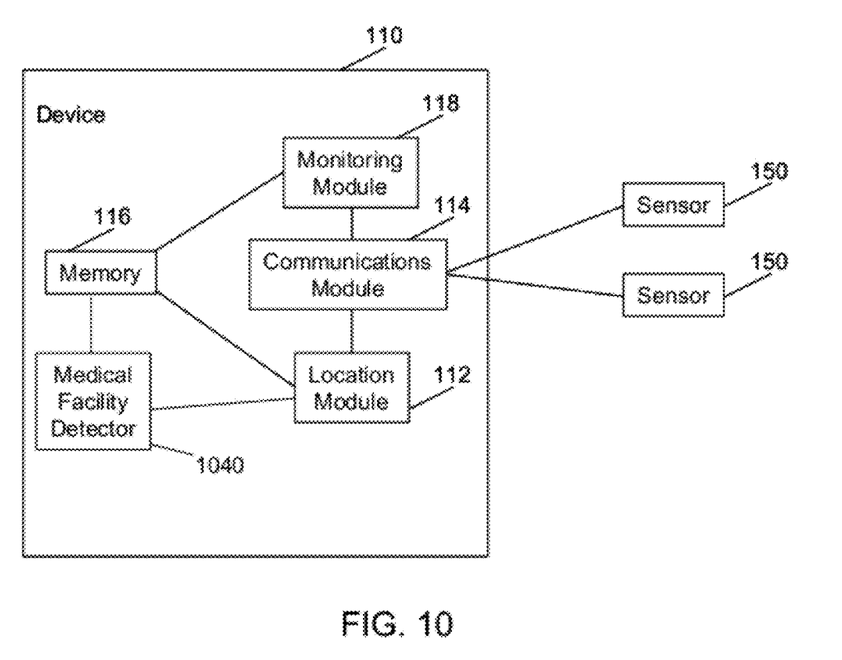
FIG. 10 illustrates yet another embodiment according to the invention.

In a further embodiment, the device further includes a medical facility detector 1040 connected to the location module 112 as illustrated in FIG. 10. The medical facility detector 1040 determines when the device is present at a medical facility based on current geospatial data translated by the location module 112 and comparison of that data to available data such as that obtained from a wide area network or a medical facility database present in the memory 116. The medical facility detector 1040 than in at least one embodiment makes the medical and geospatial data stored on the device 110 available for viewing and/or transferring from the device 110. In a further embodiment, the medical facility detector 1040 prompts the individual for allowing access to the data based on the determination that the device 110 is present at a medical facility.

In a further embodiment, the medical facility detector 1040 receives a signal detected by the communications module 114 requesting access to the stored information and in response to the request provides access to the geospatial and medical data with or without additional information stored on the device 110. Examples of the source of the signal include attachment of an external device for retrieving information from the device 110, a wireless signal transmitted from the medical facility directed at the device 110, manual entry of a code or passcode by a medical professional on the device 110, starting of an application installed on the device 110, and the entry of a biometric identifier of the individual.

An example of the usefulness of at least one of the medical facility detector embodiments is an individual is traveling abroad, becomes ill and is taken to a local hospital. The individual becomes unconscious (or there is a language barrier) and therefore unable to provide the medical professionals with any information. The hospital has no means for quickly locating or contacting the family of the individual. The health of the individual is deteriorating quickly and time is of the essence—both to save his life and to determine if he poses a threat of contagion. The individual is carrying his mobile phone (or other device 110, 410) that is equipped with at least one of the embodiments of the present invention. The medical professionals access the mobile phone which provides a complete log of the recent travel and physiological condition of the individual. The correlated physiological condition and geospatial location information of the individual provide the medical professionals with enough information to determine that the individual has likely come in contact with an outbreak or "hot spot" identified that he recently visited. Using this information, the medical professionals are able to save the life of the individual. The medical professionals are also able to quarantine the individual to prevent a localized outbreak. The present invention not only greatly assisted in saving the life of the individual but also assisted in determining that a quarantine was necessary—thereby potentially saving the lives of countless others.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium (or memory) may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 11:
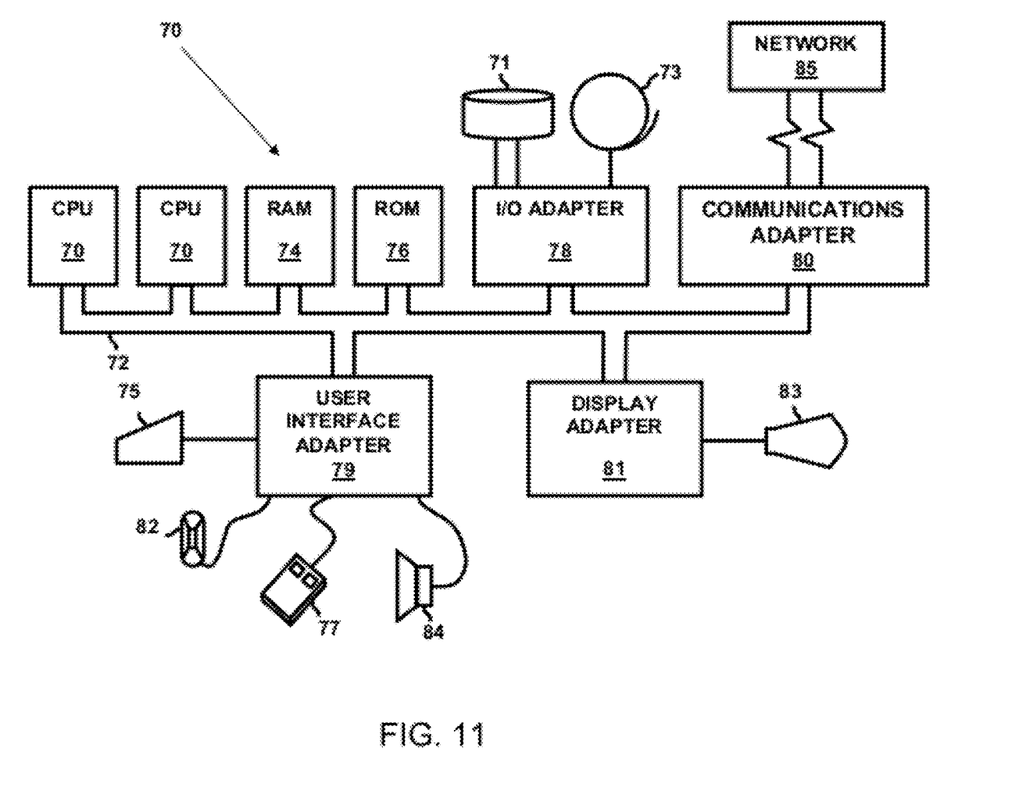
FIG. 11 illustrates a computer program product according to at least one embodiment of the invention.

Referring now to FIG. 11, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 70. The CPUs 70 are interconnected with system bus 72 to various devices such as a random access memory (RAM) 74, read-only memory (ROM) 76, and an input/output (I/O) adapter 78. The I/O adapter 78 can connect to peripheral devices, such as disk units 71 and tape drives 73, or other program storage devices that are readable by the system. The system can read the inventive instructions on the program storage devices and follow these instructions to execute the methodology of at least one embodiment of the invention. The system further includes a user interface adapter 79 that connects a keyboard 75, mouse 77, speaker 84, microphone 82, and/or other user interface devices such as a touch screen device (not shown) to the bus 72 to gather user input. Additionally, a communication adapter 80 connects the bus 72 to a data processing network 85, and a display adapter 81 connects the bus 72 to a display device 83 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The exemplary embodiments described above may be combined in a variety of ways with each other. Furthermore, the steps and number of the various steps illustrated in the figures may be adjusted from that shown.

It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

Although the present invention has been described in terms of particular embodiments, it is not limited to those embodiments. Alternative embodiments, examples, and modifications which would still be encompassed by the invention may be made by those skilled in the art, particularly in light of the foregoing teachings. The various described embodiments may be combined in a number of ways depending upon the implementation that is desired and the sensors that are available.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

We claim:

1. A method of operation of a device having memory and a communications module comprising:
    receiving at least one location signal with the communications module;
    storing geospatial data obtained at least from the at least one location signal with a time stamp in memory;
    receiving a plurality of biomedical signals over time from at least one sensor with the communications module;
    storing biomedical data from the received biomedical signal with a time stamp in memory;
    repeating the receiving at least one location signal and storing geospatial data from the at least one location signal in different geographic locations;
    determining at least one location of the device based on the geospatial data; and
    identifying at least one illness having a level of occurrence in the at least one location of the device that is above a threshold level of occurrence.

2. The method according to claim 1, further comprising determining the geographic location of the device based on contemporaneously received location signals, wherein the geographic location is the geospatial data stored.

3. The method according to claim 1, further comprising translating the location signal into a geographic location for storage as the geospatial data.

4. The method according to claim 1, further comprising receiving the series of biomedical signals from one sensor at predetermined times.

5. The method according to claim 1, further comprising:
    receiving from memory a predetermined time period for obtaining a biomedical signal from the one sensor,
    determining based on the time the last biomedical signal was received when to request the next biomedical signal from the one sensor,
    requesting the biomedical signal from the one sensor in response to the time determined to request the next biomedical signal from the one sensor.

6. The method according to claim 1, further comprising:
    determining when a new geographic location has been reached by the device,
    requesting a biomedical signal from each sensor associated with the device,
    storing the received at least one biomedical signal with a time stamp and the geographic location in memory.

7. The method according to claim 6, wherein the data is stored in a database resident in memory of the device.

8. The method according to claim 1, further comprising transferring the geospatial data, the biomedical data and associated time stamp data to an external computer.

9. The method according to claim 1, further comprising converting the biomedical signals into biomedical data representing a biomedical reading for the sensor that provided the biomedical signal.

10. The method according to claim 1, further comprising:
    correlating the biomedical readings with the geospatial data based on the respective time stamps;
    deriving at least one geographic location from the geospatial data;
    retrieving supplemental data for the at least one geographic location present in the data for time periods that the biomedical readings were gathered for that respective geographic location; and
    displaying an interface to provide the correlated data and supplemental data to a user.

11. The method according to claim 10, wherein displaying includes displaying a map showing where the individual traveled recently with each discrete geographic location illustrated having a selection element for displaying information about the individual including a name of that geographic location, time information about the geographic location, at least one biomedical reading associated with that geographic location, and supplemental data for that geographic location.

12. The method according to claim 1, wherein the at least one illness is identified with at least one health organization report.

13. The method according to claim 1, further comprising diagnosing a medical condition of a user based on the received plurality of biomedical signals and the identified at least one illness.

14. A method comprising:
    receiving a data set for an individual having geospatial data including a time stamp and biomedical readings correlated with at least one time stamp, the data set representative of recent travels of the individual;
    correlating the biomedical readings with the geospatial data with a processor based on the respective time stamps;
    retrieving supplemental data with the processor for the at least one geographic location corresponding to the geospatial data for time periods that the biomedical readings were gathered for that geographic location, wherein the supplemental data is retrieved from at least one health organization report, wherein said retrieving of the supplemental data includes conducting a search of medical databases containing information regarding health alerts, illness information for different geographic locations, and disease information for different geographic locations for information for geographic location represented by the geospatial data;
    reviewing the search results with the processor for information relevant for the time periods in which the individual associated with the received data set was present in that geographic location; and
    displaying an interface to provide the correlated data and supplemental data to a user.

15. The method according to claim 14, wherein displaying includes displaying a map showing where the individual traveled recently with each discrete geographic location illustrated having a selection element for displaying information about the individual including a name of that geographic location, time information about the geographic location, at least one biomedical reading associated with that geographic location, and supplemental data for that geographic location.

16. The method according to claim 14, wherein displaying includes displaying a plurality of locations and associated time information and biomedical readings for the individual.

17. The method according to claim 14, wherein the supplemental data includes a health alerts for the geographic locations recently visited by the individual.

18. A method of operation of a device having memory and a communications module comprising:
- receiving a plurality of biomedical signals over time from at least one sensor with the communications module;
- storing data from the received biomedical signal with a time stamp in memory;
- obtaining at least one location signal for each received biomedical signal with the communications module;
- determining geospatial data based on the at least one obtained location signal,
- storing geospatial data in memory correlated with the data from the received biomedical signal;
- repeating the receiving at least one location signal and storing geospatial data from the at least one location signal in different geographic locations;
- determining at least one location of the device based on the geospatial data;
- identifying at least one illness in the at least one location of the device;
- diagnosing a medical condition of a user based on the received biomedical signals and the identified at least one illness;
- retrieving supplemental data for geographic locations present in the data set for time periods that the biomedical readings were gathered for that respective geographic location, wherein said retrieving of the supplemental data includes conducting a search of medical databases containing information regarding health alerts, illness information for different geographic locations, and disease information for different geographic locations for information for geographic location represented by the geospatial data;
- reviewing the search results for information relevant for the time periods in which the individual associated with the received data set was present in that geographic location; and
- displaying an interface to provide the correlated data and supplemental data to a user.

19. The method according to claim 18, further comprising:
- correlating the biomedical readings with the geospatial data based on the respective time stamps;
- deriving at least one geographic location from the geospatial data.

20. The method according to claim 18, further comprising:
- correlating the biomedical readings with the geospatial data based on the respective time stamps;
- deriving at least one geographic location from the geospatial data; and
- displaying an interface to provide the correlated data to a user.

21. The method according to claim 20, wherein displaying the interface includes displaying a map showing where the individual traveled recently with each discrete geographic location illustrated having a selection element for displaying information about the individual including a name of that geographic location, time information about the geographic location, and at least one biomedical reading associated with that geographic location.

22. A method of operation of a device having memory and a communications module comprising:
- receiving at least one location signal with the communications module;
- storing geospatial data obtained at least from the at least one location signal with a time stamp in memory;
- receiving a plurality of biomedical signals over time from at least one sensor with the communications module;
- storing biomedical data from the received biomedical signal with a time stamp in memory;
- repeating the receiving at least one location signal and storing geospatial data from the at least one location signal in different geographic locations;
- determining the geographic location of the device based on contemporaneously received location signals, the geographic location is the geospatial data stored;
- translating the location signal into a geographic location for storage as the geospatial data;
- identifying at least one illness in the geographic location of the device;
- diagnosing a medical condition of a user based on the received plurality of biomedical signals and the identified at least one illness;
- retrieving supplemental data for geographic locations present in the data set for time periods that the biomedical readings were gathered for that respective geographic location, wherein said retrieving of the supplemental data includes conducting a search of medical databases containing information regarding health alerts, illness information for different geographic locations, and disease information for different geographic locations for information for geographic location represented by the geospatial data;
- reviewing the search results for information relevant for the time periods in which the individual associated with the received data set was present in that geographic location; and
- displaying an interface to provide the correlated data and supplemental data to a user.

23. The method according to claim 22, further comprising:
- receiving from memory the predetermined time period for obtaining a biomedical signal from the one sensor,
- determining based on the time the last biomedical signal was received when to request the next biomedical signal from the one sensor,
- requesting the biomedical signal from the one sensor in response to the time determined to request the next biomedical signal from the one sensor.

24. A method comprising:
- receiving a data set for an individual having geospatial data including a time stamp and biomedical readings correlated with at least one time stamp, the data set representative of recent travels of the individual;
- correlating the biomedical readings with the geospatial data with a processor based on the respective time stamps;
- retrieving supplemental data with the processor for the at least one geographic location corresponding to the geospatial data for time periods that the biomedical readings were gathered for that geographic location, the supplemental data including health alerts for the geographic locations recently visited by the individual;
- displaying an interface to provide the correlated data and supplemental data to a user, said displaying of the interface including displaying a plurality of locations and associated time information and biomedical readings for the individual; and
- diagnosing a medical condition of the individual with the processor based on the biomedical signals and the health alerts;
- retrieving supplemental data with the processor for geographic locations present in the data set for time periods that the biomedical readings were gathered for that respective geographic location, wherein said retrieving of the supplemental data includes conducting a search of medical databases containing information regarding health alerts, illness information for different geographic locations, and disease information for different geographic locations for information for geographic location represented by the geospatial data;

reviewing the search results with the processor for information relevant for the time periods in which the individual associated with the received data set was present in that geographic location; and displaying the interface to provide the correlated data and supplemental data to a user.

\* \* \* \* \*